(12) United States Patent
Ragusa

(10) Patent No.: US 7,601,268 B2
(45) Date of Patent: Oct. 13, 2009

(54) CONTINUOUS BLOOD FILTRATION AND METHOD OF USE

(75) Inventor: Michael Ragusa, Hingham, MA (US)

(73) Assignee: Haemonetics Corporation, Braintree, MA (US)

( * ) Notice: Subject to any disclaimer, the term of this patent is extended or adjusted under 35 U.S.C. 154(b) by 94 days.

(21) Appl. No.: 10/445,733

(22) Filed: May 27, 2003

(65) Prior Publication Data
US 2004/0238444 A1    Dec. 2, 2004

(51) Int. Cl.
*B01D 37/00* (2006.01)
(52) U.S. Cl. .................. 210/767; 210/137; 210/188; 210/257.1; 210/805; 604/5.01; 604/6.09; 604/406; 604/408; 604/410
(58) Field of Classification Search .............. 210/97, 210/134, 137, 257.1, 257.2, 258, 194, 195.1, 210/503–508, 645, 650, 739, 741, 767, 805, 210/188, 436, 472, 646; 604/5.01, 6.01, 604/6.09, 403–410
See application file for complete search history.

(56) References Cited

U.S. PATENT DOCUMENTS

| | | | |
|---|---|---|---|
| 3,870,042 A | 3/1975 | Viguier | |
| 3,986,506 A | 10/1976 | Garber et al. | |
| 4,086,924 A * | 5/1978 | Latham, Jr. | 604/6.04 |
| 4,596,657 A | 6/1986 | Wisdom | 210/206 |
| 4,810,378 A | 3/1989 | Carmen et al. | 210/206 |
| 4,828,543 A * | 5/1989 | Weiss et al. | 604/6.09 |
| 4,978,446 A | 12/1990 | Lobdell | 210/206 |
| 5,055,198 A | 10/1991 | Shettigar | 210/650 |
| 5,128,048 A | 7/1992 | Stewart et al. | 210/749 |
| 5,269,946 A | 12/1993 | Goldhaber et al. | 210/767 |
| 5,445,736 A | 8/1995 | Pall et al. | 210/257.1 |
| 5,527,472 A | 6/1996 | Bellotti et al. | 210/767 |
| 5,591,251 A * | 1/1997 | Brugger | 95/242 |
| 5,637,082 A * | 6/1997 | Pages et al. | 604/6.11 |
| 5,931,646 A * | 8/1999 | Nogawa et al. | 417/395 |
| 6,059,968 A | 5/2000 | Wolf, Jr. | 210/252 |
| 2005/0051486 A1* | 3/2005 | Zuk | 210/645 |

\* cited by examiner

*Primary Examiner*—Joseph W Drodge (57) ABSTRACT

The invention is directed to a system for continuously filtering a blood product including whole blood or any of its component(s), erythrocytes, leukocytes, platelets and plasma either alone or in combination. The system includes a connector for receiving the blood product, a filter coupled to the connector for filtering the received blood product, a collection bag coupled to the filter for collecting the filtered blood product, and a reservoir bag connected to the connector for temporarily storing received blood product, and providing received blood product through the connector to the filter to maintain continuity in filtration. The reservoir bag and the collection bag are suspended, the connector near or below the bottom of the collection bag, and the bottom of the reservoir bag is above the bottom of the collection bag. Also provided is a method of filtering a blood product using the continuous blood filtration system.

59 Claims, 4 Drawing Sheets

CONTINUOUS BLOOD FILTRATION AND METHOD OF USE

TECHNICAL FIELD AND BACKGROUND ART

The present invention generally relates to blood filtration systems and methods. More particularly, the invention relates to a system for continuously filtering a blood product passed through the system, and to a method of use of the system.

Most of the whole blood collected from donors today is not typically stored as to whole blood and used for transfusions. Instead, the blood is first separated into its components, including erythrocytes (red blood cells), leukocytes (white blood cells), platelets and plasma, and the components are then individually stored and used to treat specific diseases and disease states. Erythrocytes, for example, are used to treat anemia. Platelets are used to control diseases such as thrombocytopenic bleeding, and plasma can be used as either a volume expander, or as a source for clotting factor VIII for use in the treatment of hemophilia.

Blood collection systems in the art typically include multiple plastic bags interconnected by multiple plastic tubes. Such systems include nonsterile systems that are open to the atmosphere, and sterile systems that are closed to communication with the atmosphere. Open collection systems are subject to government regulation that controls the plastic materials that are used to fabricate the multiple interconnected blood bags. They are also subject to government regulations that limit the maximum storage periods for blood components collected using these systems.

Closed blood collection systems permit blood storage for extended periods of time and have gained wider acceptance. Erythrocytes, for example, collected can be stored for up to forty-two days, depending on the type of anticoagulant and storage container used. Platelets can be stored for up to five days, depending on the type of storage container used. Plasma may be frozen and stored for even longer periods of time. Closed storage systems are also more reliable because the systems provide a more sterile environment that maximizes the possible storage period and minimizes the presence of impurities or other materials that may cause undesired side effects to recipients.

Closed blood collection systems known in the art typically include a number of sealed blood compatible bags that are connected together by blood compatible conduits, and include a filter disposed on a conduit between any two bags. Blood component collection according to these systems is accomplished by collecting whole blood from a donor or a blood source in a first of these bags and separating the blood into its components by squeezing the blood from the first bag through the conduit and filter into a second bag. This method of filtration is repeated until the desired filtered blood product is attained. Such blood collection systems are exemplified by U.S. Pat. No. 3,986,506 issued to Garber, et al., U.S. Pat. No. 4,596,657 issued to Wisdom, and U.S. Pat. No. 5,527,472 issued to Bellotti, et al. A similarly configured closed blood collection system that utilizes the force due to gravity to accomplish the steps of separation by filtration is exemplified by U.S. Pat. No. 6,059,968 issued to Wolf, Jr. It is unknown whether such systems are, indeed, effective in accomplishing the stated filtration objectives. Regardless, however, such systems are undesirable as they fail to permit or enable the continuous filtration of blood to produce the desired blood product. They are also complex in construction, cumbersome to use, and are typically expensive to produce.

Figure 1:
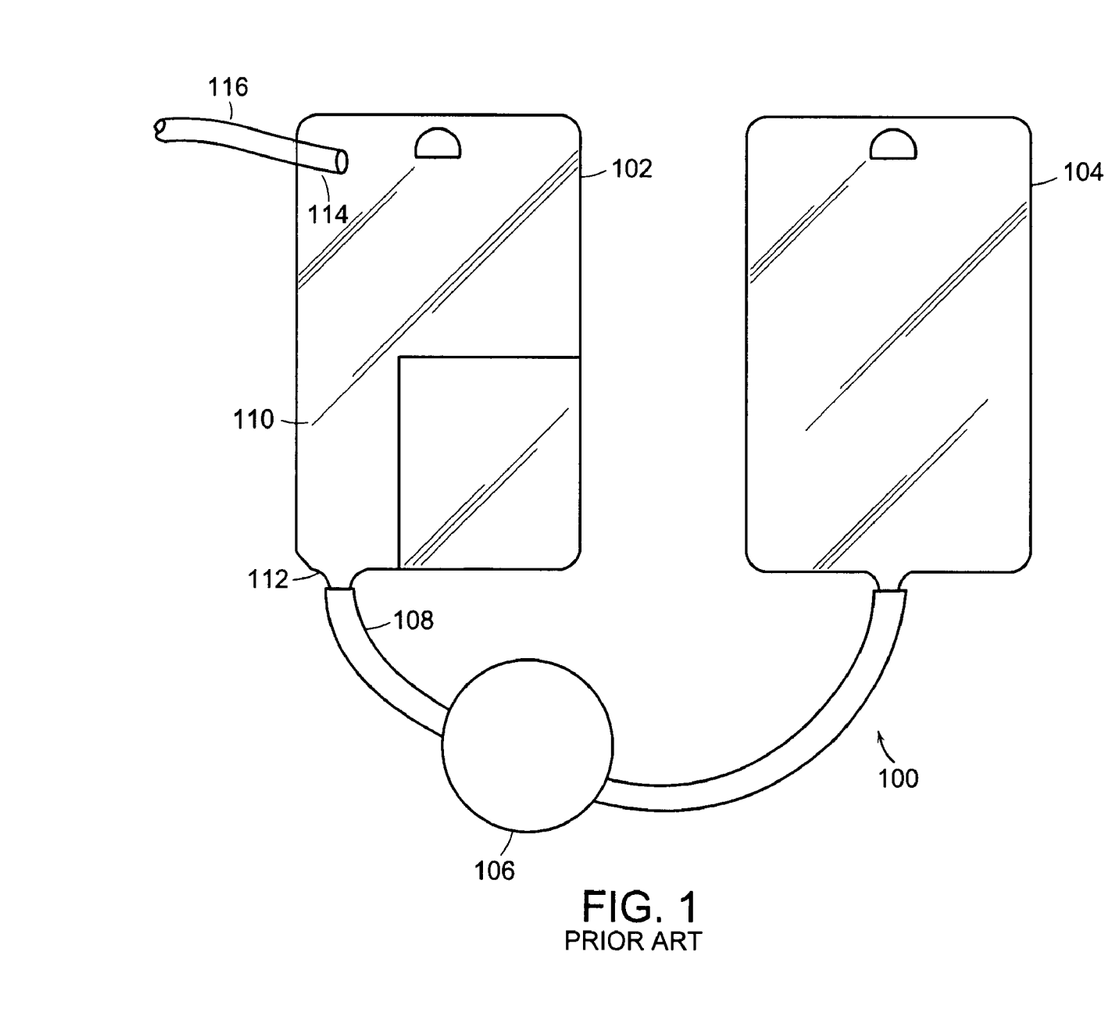
FIG. 1 is a block diagram of a prior art blood filtration system.

FIG. 1 illustrates one type of continuous filtration closed blood collection system which utilizes multi-bag collection concept. The system shown in FIG. 1 is the model 994CF-blood collection system manufactured by Haemonetics Corporation of Braintree, Mass., USA. The 994CF system is adapted for filtering leukocytes from platelet rich plasma to produce a purer or more concentrated platelet product. The platelet rich plasma is typically provided to the 994CF system in cycles during apheresis, in which whole blood is drawn from a donor and separated into its constituent components such that one or more components are collected while the remaining components are returned to the donor. As shown in FIG. 1, the 994CF system 100 includes a reservoir bag 102, a platelet collection bag 104, a filter 106, and a conduit 108 that connects the reservoir bag 102 to the platelet collection bag 104.

The reservoir bag 102 includes a top or "chimney" port 114 for receiving the platelet rich plasma through a conduit 116, a channel 110 vertically disposed from a midpoint of the bag to its bottom, and an outlet port 112 located at the bottom of the channel 110. Filter 106 is a leukoreduction filter, which is positioned on the conduit 108 between the reservoir bag 102 and the platelet collection bag 104. Leukoreduction filters have two qualities that filtration methods must handle. First, once the filter 106 is primed to (wetted for the first time), it will no longer pass air. Any air that is introduced into the filter 106 will become lodged against the filtering membrane, and effectively reduce the filtering capacity of the filter 106. Large amounts of air will clog the filter 106 entirely and stop flow. Second, the flow rate of the solution to be filtered affects the efficiency of the filter 106. The channel 110 has a volume capacity of approximately 15 ml. Typically, both the platelet collection bags 104 and the reservoir bag 102 are hung on the same IV pole.

At the beginning of the first platelet collection cycle with the 994CF system 100, the conduit 108, the reservoir bag 102, the leukoreduction filter 106 and the platelet collection bags 104 are empty and dry. As the first platelets are expressed into the reservoir bag 102, a rivulet of fluid travels down the vertical channel 110 and into the leukoreduction filter 106. The volume of fluid in the rivulet is insufficient to fill the vertical channel 110. After several seconds, the inherent resistance of the filter 106 causes the fluid to back up into the vertical channel 110. Fluid fills the vertical channel 110, causing a fluid height difference between the full vertical channel 110 and the empty platelet collection bag 104. Gravity applies a force to the fluid until the fluid level in the vertical channel 110 equals the fluid level in the platelet collection bag 104. As the reservoir bag 102 and the platelet collection bag 104 are typically hung on a single IV pole at similar heights, there is always some fluid held back in the vertical channel 110. This prevents any air from being introduced into the filter 106 in subsequent cycles. The narrow dimension of the vertical channel 110 ensures that there is initially a fluid height difference between the reservoir bag 102 and the platelet collection bag 104 in every cycle.

The platelet collection process during apheresis is discontinuous. Each cycle produces between 20 and 70 ml of platelet product that is expressed through the conduit 108 and deposited into the reservoir bag 102. The delay between subsequent platelet collection cycles is typically 12 to 15 minutes. After the final platelet collection cycle, the vertical channel 110 holds approximately 10 to 15 ml of fluid. Thereafter, the operator removes the platelet collection bag 104 from the IV pole, and lowers it relative to the reservoir bag 102 to allow the volume of fluid remaining in the channel 110 to be filtered.

Though more advantageous than other multi-bag blood collection systems in the art, the 994CF system 100 also presents disadvantages. During the first cycle, for example, the rivulet of fluid introduced into the reservoir bag is insufficient to fill the vertical channel 110. This allows a mix of fluid and air to enter the filter 106, potentially clogging a portion of the filter 106. The structure of the reservoir bag also buffers or reduces the pressure (priming pressure) of fluid flowing to the dry filter. The reduced fluid pressure renders it more difficult to ensure that the entire filter is fully wetted, or primed at the outset. After the final cycle, the flow rate of the fluid through the filter 106 depends on the rate at which the operator lowers the platelet collection bag 104. Processing the final 10 to 15 ml of fluid through the filter 106 at a high rate can dislodge white blood cells from the filter 106. In addition, the chimney port 114 of the reservoir bag 102 is difficult to package efficiently, as kinks may form where the conduit 116 is bonded to the chimney port 114. Moreover, production of the reservoir bag 102 is more expensive than the production of a typical bag as the chimney port 114 requires additional manufacturing steps.

SUMMARY OF THE INVENTION

In accordance to one embodiment of the invention, a system and method for continuously filtering a blood product is presented. The system includes a filter and a conduit. The conduit has an inlet for receiving the blood product from a blood product source and an outlet for delivering the blood product to the filter. The conduit is in fluid communication with a vessel for accommodating blood product flow rate variation between the inlet and the filter. The conduit is sized so as to prevent an air-blood mix from entering into the filter once the blood product is received by the filter, and/or to provide a blood product flow rate that results in the predetermined priming pressure at the filter.

In embodiments related to the above-described embodiments, the conduit may have a cross-section dimensioned such that, during priming of the filter, blood product flow rate is sufficient to fill the cross-section. The inlet may be positioned in the conduit between the vessel and the filter. Alternatively, the vessel may be positioned in the conduit in series between the inlet and the filter. The predetermined pressure may be based at least on physical and material characteristics of the vessel. The vessel may have an adjustable volume so as to regulate pressure applied to the filter. For example, the vessel may have an outer surface and the volume of the vessel can be contracted by mechanically applying pressure to the outer surface. The vessel may have a volume that changes, such as by expanding or contracting, so as to accommodate variations in blood product flow rate between the inlet and the filter.

In accordance with another embodiment of the invention, a system for continuously filtering a blood product includes a three-way connector for receiving the blood product, a filter in fluid communication with the connector for filtering the blood product, a collection bag for collecting blood product passing through the filter, and a reservoir bag also coupled to the connector and configured to temporarily receive any blood product that backs up from the filter through the connector during the filtration process. The reservoir bag of the system enables continuous blood product filtration by collecting the blood product that backs-up from the filter and holding it until the filter is ready to receive it. The filter, the collection bag and the reservoir bag are each in sealed communication with the connector, and define a closed, continuous blood filtration system.

The connector communicates blood product through the filtration system. The connector includes a first connector inlet for receiving the blood product from a blood product source, a second connector inlet and a connector outlet. The filter includes a filter inlet for receiving the blood product from the connector, and a filter outlet for communicating the filtered blood product to the collection bag. The reservoir bag is fluidly connected to the second connector inlet, and receives the blood product that backs-up through the second connector inlet as it is coursed through the connector to the filter. The reservoir bag provides the collected blood product through the second inlet to the connector and the filter to maintain continuity in filtration when blood product is not received through the first connector inlet. The reservoir and collection bags are suspended such that the connector is below the bottom of the collection bag and the bottom of the reservoir bag is above the bottom of the collection bag. In other embodiments, the connector may be proximate to, or slightly above, the bottom of the collection bag, but below the fluid level in the collection bag after the first cycle.

In related embodiments of the invention, the system preferably includes a series of conduits disposed between the connector, the filter, the reservoir bag and the collection bag for fluidly communicating the blood product through the system. Each conduit of the system is configured to eliminate air from the system, and to maintain constancy in the flow rate of the blood product coursing through the system. In this system, the connector is a Y connector, the filter is a leukoreduction filter, the reservoir and the collection bags are typically hung from the same IV-pole, and blood platelets are filtered to produce a purer platelet product.

Also provided is a method of filtering a blood product using the system for continuously filtering blood products. The method invention includes the steps of introducing blood product to the system, filtering the blood product through the system, and collecting the filtered blood product in the collection bag.

In accordance with yet another embodiment of the invention, a system for continuously filtering a blood product includes a filter and a conduit, the conduit having an inlet for receiving the blood product from a blood product source and having an outlet for delivering the blood product to the filter. A portion of the conduit has a variable cross-section for accommodating blood product flow rate variation between the inlet and the filter. The conduit is sized so as to prevent an air-blood mix from entering into the filter once the blood product is received by the filter, and/or to provide a blood product flow rate that results in the predetermined priming pressure at the filter.

In related embodiments of the invention, the portion of the conduit is capable of expanding or contracting. The portion of the conduit may be made of an elastic, stretchable, and resilient material.

In accordance with still another embodiment of the invention, a method of continuously filtering a blood product is presenting that includes receiving a blood product from a blood source at a source flow rate. The blood product is transported to a filter via a conduit such that an air-blood mix is precluded from entering the filter once the blood product is received by the filter, and/or to provide a blood product flow rate that results in the predetermined priming pressure. The blood product is filtered via the filter, the filter having a filter flow rate. The filtered blood is collected into a collection bag.

A portion of the conduit has a variable cross-section for accommodating blood product flow rate variation between the inlet and the filter.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

A system for continuous filtration of a blood product is presented. In accordance with the present invention, the phrase "blood product" includes whole blood or any of its component(s), erythrocytes, leukocytes, platelets and plasma either is alone or in combination. The present invention may be used advantageously as a continuous filtration system that serves as a part of apheresis device to leukoreduce platelet rich plasma to produce a "purer" platelet product.

The system generally includes a filter and a conduit. The conduit has an inlet for receiving the blood product from a blood product source and an outlet for delivering the blood product to the filter. The conduit is sized so as to prevent an air-blood mix from entering into the filter once the blood product is received by the filter. In other embodiments, the conduit may be sized so as to apply a predefined priming pressure to the filter.

Figure 2:
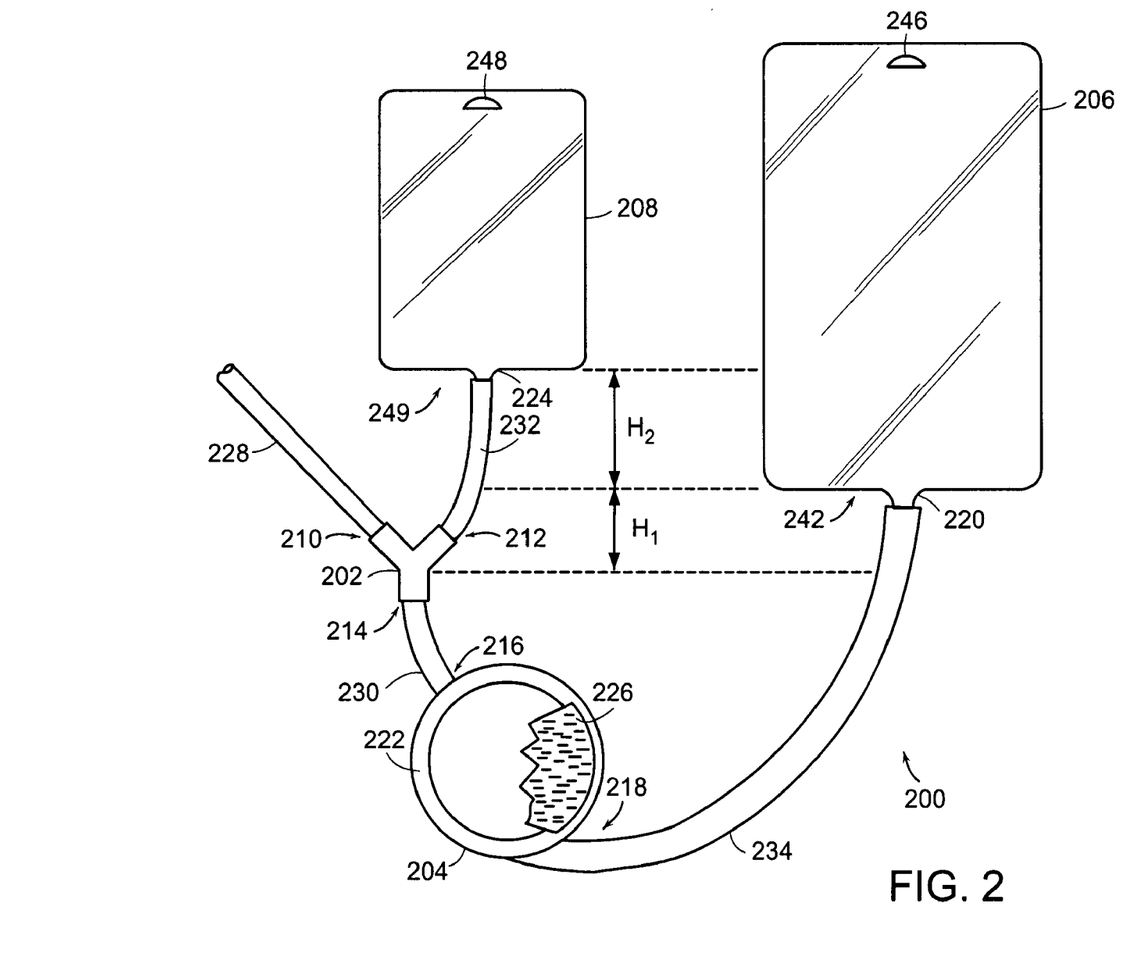
FIG. 2 is a block diagram of a blood filtration system in accordance with the present invention.

FIG. 2 is an illustration of a continuous blood filtration system 200, in accordance with one embodiment of the present invention. The system 200 includes a three-way connector 202 for receiving a blood product, a filter 204 for filtering the product, a collection bag 206 that collects the filtered blood product, and a reservoir bag 208 for temporarily storing any blood product that backs up through the connector 202 during the filtration process. Connector 202 includes a first connector inlet 210 for receiving the blood product, a second connector inlet 212 and a connector outlet 214. Filter 204 includes a filter inlet 216 for receiving blood product from the connector outlet 214, a filter medium 226 for filtering the product and a filter outlet 218. Collection bag 206 collects filtered blood product from the filter outlet 218. Reservoir bag 208 is connected to the second connector inlet 212 and temporarily stores blood product that backs up through the second connector inlet 212 as it passes from the connector inlet 210 to the connector outlet 214. The reservoir bag 208 provides collected blood product through the second connector inlet 202 to the filter 204 to maintain continuity in filtration when blood product is not received through the first connector inlet 210.

The system 200 of the present invention constitutes a sterile environment, according to applicable U.S. standards. The filter 204, the collection bag 206 and the reservoir bag 208 are each in sealed fluid communication with the connector 202 to define a closed, continuous filtration system. The system 200 remains closed during processing to assure that the longest authorized storage intervals can be used for the blood components collected. In use, the system 200 of the present invention is suspended from a stand (not shown), such as a conventional IV pole, in a manner that facilitates the flow of blood product through the filter 204 and into the collection bag 206. After use, the system 200 is properly disposed of, also in accordance with applicable U.S. standards.

As illustrated in FIG. 2, the three-way connector 202 is preferably integrally formed and defines a "Y" connector, wherein the two branches of the "Y" form the first and second connector inlets 210, 212 and the trunk forms the connector outlet 214. It will be recognized that the three-way connector 202 may also be formed of a series of components that are assembled to provide the branched fluid flow path defined by connector 202. Similarly, it is recognized that the connector 202 may have another similar configuration, such as a "T" connector. Still other embodiments of the three-way connector 202 are equally foreseeable.

Filter 204 includes a housing 222 and a filtration medium 226 which is suited for filtering one blood component, such as erythrocytes, leukocytes, or platelets, from plasma or from another blood component. Filter housing 222 encases the filter medium 226 to preserve the integrity and sterility of the filtration environment. The filter housing 222 is preferably made of a rigid plastic material such as polyvinyl chloride. The filtration medium 226 preferably consists of a fibrous medium such as cotton, wool, cellulose acetate or any other synthetic fibers, such as polyester, polyamides and the like. As set forth above, according to the present invention, filter 204 is preferably a leukoreduction filter for leukoreducing platelet rich plasma, and the system 200 is incorporated into an apheresis system to automatically produce a "purer" platelet product.

Collection bag 206 includes a bottom 242, a hanger opening 246 to permit the bag to be hung from the stand, and a collection inlet 220 disposed proximate to the bottom 242 of the bag 206 for receiving filtered blood product from the filter outlet 218. Reservoir bag 208 similarly includes a bottom 244, a hanger opening 248 for hanging the bag 208 from the stand, and a reservoir inlet 224 disposed proximate to bottom 244 for receiving blood product that backs up through the second connector inlet 212. As shown in FIG. 2, the reservoir bag 208 and the collection bag 206 are suspended from the stand, the connector 204 is positioned below the bottom 242 of the collection bag 206, by some height H1, and the bottom 244 of the reservoir bag 208 is positioned above the bottom 242 of the collection bag 206, by some height H2. In other embodiments, the connector 204 may be positioned above or proximate the bottom 242 of the collection bag 206, but below the fluid level in the collection bag 206 after the first cycle.

The collection and reservoir bags are made of a medical grade plasticized polyvinyl chloride plastic. However, other grades and types of flexible plastic materials can be used. The volume of the reservoir bag, at a minimum, may be advantageously sufficient to hold at least one cycle of collected product. There is no maximum volume of the reservoir bag 208, but its length may advantageously be made be less than that of the collection bag 206 (assuming that they are hung from the same pole).

As further illustrated in FIG. 2, the blood filtration system 200 of the present invention preferably includes a series of conduits for receiving blood product and communicating the product through the closed continuous system 200 to the collection bag 206.

More specifically, the system 200 includes a first conduit 228 coupled to the first connector inlet 210 for fluidly communicating blood product from a source such as a blood donor or vessel such as a blood bag containing blood product, to the first connector inlet 210. A second conduit 230 is coupled to the connector outlet 214 and the filter inlet 216 for fluidly communicating blood product from the connector 202 to the filter 204. A third conduit 232 is coupled to the reservoir inlet 224 and the second connector inlet 212 for fluidly communicating blood product from connector 202 to reservoir bag 208. A fourth conduit 234 is coupled to the filter outlet 218 and the collection inlet 220 for fluidly communicating filtered blood product from the filter 204 to the collection bag 206. The first, second and third conduits 228, 230, and 232 are preferably dimensioned to preclude air infiltration into the filter 204 once the system 200 is in operation.

The conduits are made of a medical grade of a plastic material that is blood compatible, flexible, translucent and sterilized. The conduits, accordingly, are preferably formed of polyvinyl chloride, polyester, polyurethane, polyolefin, or a blend of these materials. However, other flexible, medical grade plastic materials can be used.

As set forth herein, the blood filtration system 200 of the present invention provides several distinct advantages over the prior art.

A first advantage is provided by placement of the connector 202 between the reservoir bag 208 and the filter 204. The positioning of connector 202 between the bag 208 and the filter 204 eliminates the need for the chimney port of the reservoir bag above described Haemonetics system. The resulting reservoir bag 208 is easier to package and less expensive to manufacture.

A second advantage is provided by disposing conduit 232 between the reservoir bag 208 and the connector 202 to create the difference in fluid height between the reservoir bag 208 and the collection bag 206. The use of the conduit 232 instead of the vertical channel decreases the hold-up volume at the end of the procedure from 10-15 mL to approximately 1 mL. Though the variation in flow rate according to the present invention may still be dependent on the operator technique, the risk is reduced because the volume involved becomes very low. Thus, conduit 232 eliminates the need for the narrow vertical channel of prior art devices.

The dimensioning of conduits 228, 230, 232 provide a third advantage. The conduits 228, 230, 232 are dimensioned so that the fluid flow rate through the conduits during the first collection cycle is sufficient to fill a cross-section of the conduits 228 and 230. This prevents air from mixing with fluid and entering the filter 204 through the conduit 230. Conduit 232 is also dimensioned to ensure that the Y-connector 202 is below the bottom 242 of the collection bag 206 when the collection bag 206 and the reservoir bag 208 are hung on an IV pole(s). This prevents any air in reservoir bag 208 from entering the filter 204 during subsequent cycles. In other embodiments, conduit 232 may be dimensioned so that Y-connector 202 is proximate to, or slightly above, the bottom 242 of the collection bag, but below the fluid level in the collection bag 206 after the first cycle.

A further advantage is found in directly communicating the fluid entering the system into the filter. The direct communication of the fluid enables an increased priming pressure which, during the first filtration cycle eliminates the buffering effect noted in prior art systems and better ensures that the filter material is entirely wetted or primed.

Still other advantages are provided by the method for filtering a blood product using this blood filtration system 200.

Figure 3:
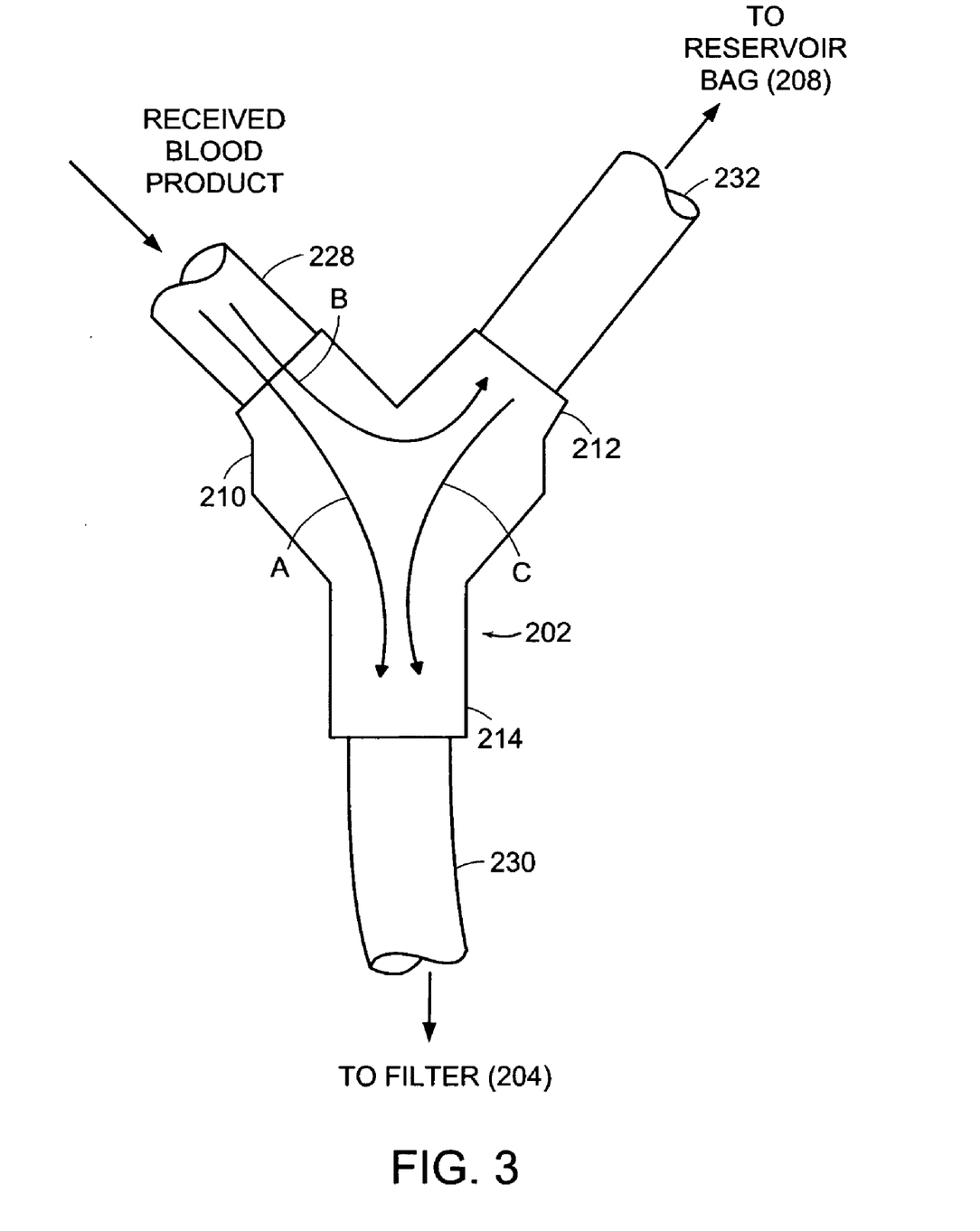
FIG. 3 is an enlarged view of the three-way connector of the present invention, showing the flow path of received blood product through the connector.

According to this method, a blood product is filtered by performing the steps of introducing the blood product to the system 200 of the present invention, filtering the blood product, and collecting the filtered blood product in the collection bag 206. Specifically, platelet rich plasma is introduced through the first conduit 228 to the Y connector 202 through first conduit inlet 210. The platelet rich plasma flows through the Y-connector outlet 214 and into the filter 204 as shown by arrow A (FIG. 3). Since the filter 204 cannot process the platelet rich plasma at the rate at which it is provided, excess plasma flows through the second connector inlet 212 and into the reservoir bag 208 (arrow B). This filtration and temporary collection process continues until the external supply of platelet rich plasma is exhausted.

When the platelet supply is suspended (e.g., pending the next collection cycle), the platelet rich plasma continues to flow from the reservoir bag 208, through the filter is 204 via connector 202 (arrow C) and into the collection bag 206 until the level of fluid between the two bags 206, 208 is the same. By virtue of the small diameter of the conduits 228, 230, 232 leading to the filter inlet 216, air is prevented from contacting the filter medium 226 once it is "wet." When collection of platelets is completed, the operator removes collection bag 206 from the stand and lowers it relative to reservoir bag 208 in order to filter and recover any platelets remaining in the conduit 232 and/or bag 208. The use of the small diameter conduit 232 upstream of the filter 204, in conjunction with the positioning of the reservoir bag 208 relative to the collection bag 206, minimizes the amount of platelet rich plasma to be filtered after the last collection cycle, and reduces the chance of overloading or overpowering the filter 204.

Figure 4:
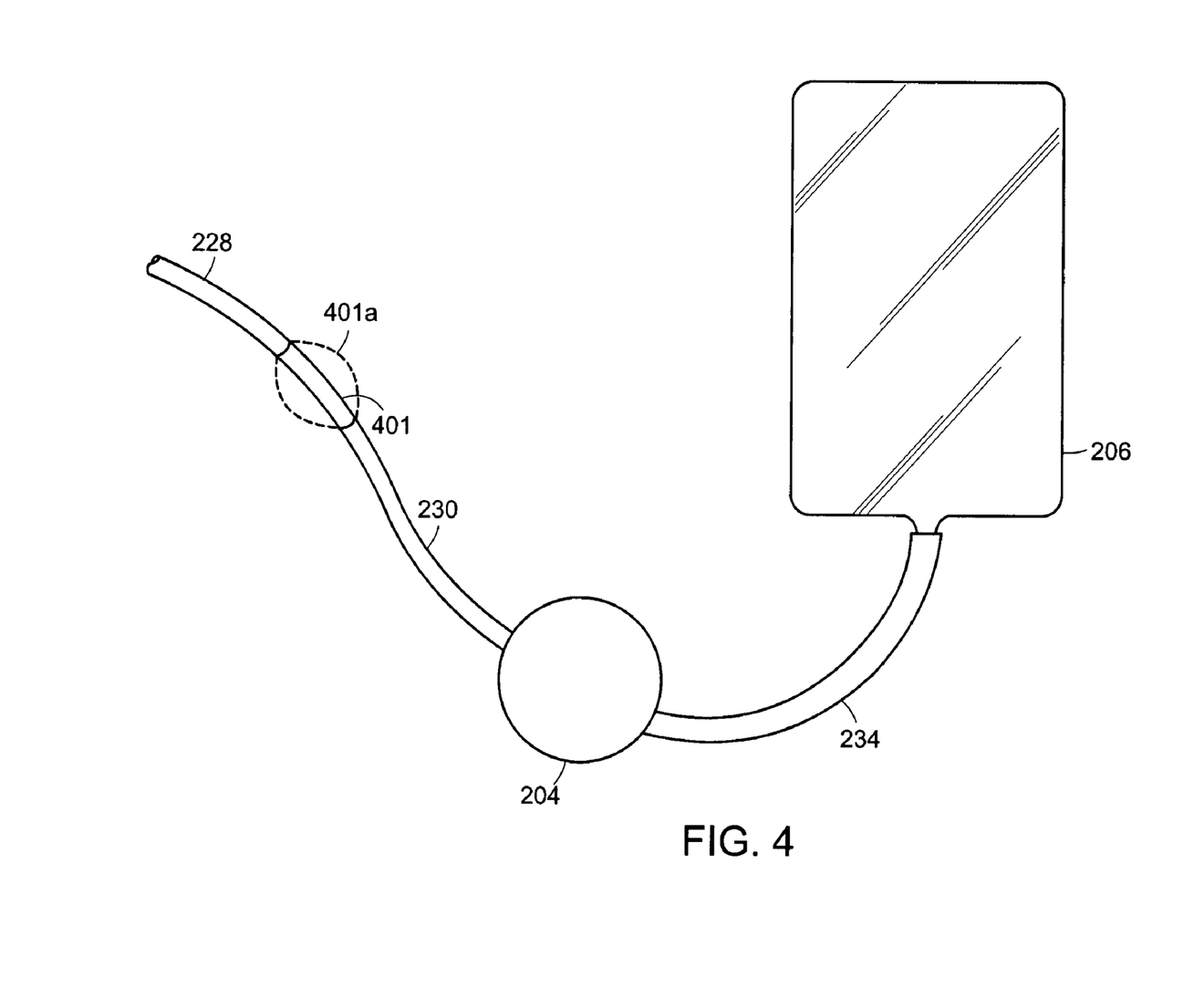
FIG. 4 is a block diagram of a blood filtration system in which a reservoir is in series with a blood inlet and filter, in accordance with one embodiment of the invention.

In accordance with other embodiments of the invention, the reservoir 401 may be positioned in the conduit in series between the inlet 228 for receiving blood and the filter 204, as shown in FIG. 4. Initially, the cross-sectional area of the reservoir 401 may be substantially the same as the cross-sectional area of the conduit, with the conduit being sized, as discussed above, so that an air-blood mix does not enter the filter once the blood product is received by the filter and/or the appropriate priming pressure is received at the filter 204. However, the physical and material characteristics of the reservoir allow the cross-sectional area and volume of the reservoir 401 to change such as by contracting or expanding (as shown, for example, by line 401*a*) so as to accommodate variations in blood product flow rate between the inlet and the filter. The reservoir 401 in such embodiments may be made of an elastic, stretchable and resilient material, such as, without limitation, rubber.

The volume of the reservoir in the above-described embodiments may be adjustable so as to regulate the pressure applied to the filter. For example, pressure may be applied to the outer surface of the reservoir so as contract the volume of the vessel. A predetermined pressure may be applied to the filter based at least on physical and material characteristics of the vessel, such as the elasticity and/or resiliency of the vessel material.

The described embodiments of the invention are intended to be merely exemplary and numerous variations and modifications will be apparent to those skilled in the art. All such variations and modifications are intended to be within the scope of the present invention as defined in the appended claims.

What is claimed is:

1. A system for continuously filtering a blood product comprising:
   a filter having a filter inlet and a filter outlet communicating filtered blood to a blood product collection bag and
   a conduit having an inlet for receiving the blood product from a blood product source and having an outlet for delivering the blood product to the filter, the conduit in fluid communication with and joined to an adjustable volume vessel by a connector located between the inlet and filter for accommodating blood product flow rate variation between the inlet and the filter, the conduit sized so as to prevent an air-blood mix from entering into the filter once the blood product is received by the filter wherein the vessel and the collection bag each include a bottom, the vessel and the collection bag being constructed and dimensioned to enable positioning during filtration such that the connector is below the bottom of the collection bag, and the bottom of the vessel is above the bottom of the collection bag.

2. The system according to claim 1, wherein the conduit has a cross-section dimensioned such that, during priming of the filter, blood product flow rate is sufficient to fill the cross-section.

3. The system according to claim 1, wherein the inlet is positioned in the conduit between the vessel and the filter.

4. The system according to claim 1, wherein the vessel is positioned in the conduit in series between the inlet and the filter.

5. The system according to claim 1, wherein the vessel has an adjustable volume so as to regulate pressure applied to the filter.

6. The system according to claim 5, wherein the vessel has an outer surface and the volume of the vessel can be contracted by mechanically applying pressure to the outer surface.

7. The system according to claim 1, wherein a predetermined pressure is applied to the filter, the predetermined pressure based at least on physical and material characteristics of the vessel.

8. The system according to claim 1, wherein the vessel has a volume that changes to accommodate variations in blood product flow rate between the inlet and the filter.

9. The system according to claim 8, wherein the volume expands.

10. The system according to claim 8, wherein the volume contracts.

11. A system for continuously filtering a blood product, the system comprising:
    a filter having a filter inlet and a filter outlet for communicating filtered blood to a blood product collection bag and having a predetermined priming pressure for initially receiving the blood product; and
    a conduit having an inlet for receiving the blood product from a blood product source, and an outlet for delivering the blood product to the filter, the conduit in fluid communication with and joined to an adjustable volume vessel by a connector between the inlet and the filter for accommodating blood product flow rate variation between the inlet and the filter, the conduit sized so as to provide a blood product flow rate that results in the predetermined priming pressure at the filter
    wherein the vessel and the collection bag each include a bottom, the vessel and the collection bag being constructed and dimensioned to enable positioning during filtration such that the connector is below the bottom of the collection bag, and the bottom of the vessel is above the bottom of the collection bag.

12. A system according to claim 11, wherein the inlet is positioned in the conduit between the vessel and the filter.

13. The system according to claim 11, wherein the vessel is positioned in the conduit in series between the inlet and the filter.

14. The system according to claim 11, wherein the vessel has an adjustable volume so as to regulate pressure applied to the filter.

15. The system according to claim 14, wherein the vessel has an outer surface and the volume of the vessel can be contracted by mechanically applying pressure to the outer surface.

16. The system according to claim 11, wherein the vessel has a volume that changes to accommodate variations in blood product flow rate between the inlet and the filter.

17. The system according to claim 16, wherein the volume expands.

18. The system according to claim 16, wherein the volume contracts.

19. A method of continuously filtering a blood product, the method comprising:
    receiving a blood product from a blood source at a source flow rate;
    transporting the blood product to a filter via a conduit so that an air-blood mix is precluded from entering the filter once the blood product is received by the filter;
    filtering the blood product via the filter to a collection bag, the filter having a filter flow rate;
    directing overflow created by a difference between the source flow rate and the filter flow rate to an adjustable volume vessel in communication with the conduit and joined between the blood source and the filter by a connector, the vessel having a volume; and
    collecting the filtered blood into a collection bag,
    wherein the vessel and the collection bag each include a bottom, the vessel and the collection bag being constructed and dimensioned to enable positioning during filtration such that the connector is below the bottom of the collection bag, and the bottom of the vessel is above the bottom of the collection bag.

20. The method according to claim 19 further comprising regulating pressure to the filter based at least on physical and material characteristics of the vessel.

21. The method according to claim 20, wherein regulating pressure to the filter includes mechanically adjusting the volume.

22. The method according to claim 19, wherein the conduit has an inlet for receiving the blood product from the blood product source, the inlet positioned in the conduit between the filter and the vessel.

23. The method according to claim 19, wherein the conduit has an inlet for receiving the blood product from the blood product source, the vessel is positioned in the conduit in series between the inlet and the filter.

24. The method according to claim 19, wherein the volume of the vessel changes to accommodate the difference.

25. A method of continuously filtering a blood product, the method comprising:
    receiving a blood product from a blood source at a source flow rate;
    transporting the blood product to a filter via a conduit, the filter having a predetermined priming pressure for receiving the blood product, the conduit providing a blood product flow rate that results in the predetermined priming pressure;
    filtering the product via the filter to a collection bag, the filter having a filter flow rate;
    directing overflow created by a difference between the source flow rate and the filter flow rate to an adjustable volume vessel in communication with the conduit and joined between the blood source and the filter by a connector, the vessel having a variable volume; and collecting the filtered blood into a collection bag,
wherein the vessel and the collection bag each include a bottom, the vessel and the collection bag being constructed and dimensioned to enable positioning during filtration such that the connector is below the bottom of the collection bag, and the bottom of the vessel is above the bottom of the collection bag.

26. The method according to claim 25, wherein the conduit has an inlet for receiving the blood product from the blood product source and the inlet is positioned in the conduit between the filter and the vessel.

27. The method according to claim 25, wherein the conduit has an inlet for receiving the blood product from the blood product source and the vessel is positioned in the conduit in series between the inlet and the filter.

28. The method according to claim 25, further comprising mechanically adjusting the volume so as to regulate pressure applied to the filter.

29. The method according to claim 25, wherein the volume of the vessel changes to accommodate the difference.

30. A system for continuously filtering a blood product comprising:
a connector having a first inlet for receiving the blood product, a second inlet and an outlet;
a filter having a filter inlet, the filter coupled to the connector outlet;
a collection bag coupled to the filter for collecting filtered blood product; and
a reservoir bag connected to the second connector inlet for temporarily storing received blood product, and providing the blood product through the connector to the filter to maintain continuity in filtration
wherein the reservoir bag and the collection bag each include a bottom, the reservoir bag and the collection bag being constructed and dimensioned to enable positioning during filtration such that the connector is below the bottom of the collection bag, and the bottom of the reservoir bag is above the bottom of the collection bag.

31. The system of claim 30 wherein the connector is a Y connector, the filter is a leukoreduction filter and the blood product comprises blood platelets.

32. The system of claim 30 wherein the filter includes a housing and a filter medium disposed within the housing.

33. The system of claim 32 wherein the filter medium is selected from the group consisting of cotton wool, cellulose acetate and synthetic fibers.

34. The system of claim 30 further comprising a first conduit disposed on the first connector inlet for fluidly communicating the received blood product to the first connector inlet, and a second conduit disposed between the connector outlet and the filter inlet.

35. The system of claim 34 further comprising a third conduit disposed between the reservoir bag and the second connector inlet for fluidly communicating blood product from and back into the connector through the second connector inlet.

36. The system of claim 34 further comprising a fourth conduit disposed between a filter outlet and the collection bag for fluidly communicating filtered blood product from the filter to the collection bag.

37. The system of claim 34 wherein the first and second conduits are dimensioned to preclude air infiltration into the filter once the system is in operation.

38. The system of claim 30 wherein the reservoir bag and the collection bag each define a bottom, the reservoir bag and the collection bag are suspended, the connector is below the bottom of the collection bag, and the bottom of the reservoir bag is above the bottom of the collection bag.

39. A system for continuously filtering a blood product comprising;
a connector having a first inlet for receiving the blood product, a second inlet and an outlet;
a first conduit connected to the first connector inlet for fluidly communicating received blood product to the first connector inlet;
a filter having a filter inlet, the filter coupled to the connector outlet;
a collection bag coupled to the filter for collecting filtered blood product;
a second conduit disposed between the connector outlet and the filter inlet; and
a reservoir bag connected to the second connector inlet for temporarily storing received blood product, and providing the blood product through the connector to the filter to maintain continuity in filtration,
wherein the reservoir bag and the collection bag each include a bottom, the reservoir bag and the collection bag being constructed and dimensioned to enable positioning during filtration such that the connector is below the bottom of the collection bag, and the bottom of the reservoir bag is above the bottom of the collection bag.

40. The system of claim 39 wherein the connector is a Y connector, the filter is a leukoreduction filter and the blood product comprises blood platelets.

41. The system of claim 39 wherein the collection bag includes a bottom, and the connector is above the bottom of the collection bag when the collection bag is suspended, but below the fluid level in the collection bag after a first cycle.

42. The system of claim 39 further comprising a third conduit disposed between the reservoir bag and the second connector inlet for fluidly communicating the received blood product from and back into the connector through the second connector inlet.

43. The system of claim 39 further comprising a fourth conduit disposed between the filter outlet and the collection bag for fluidly communicating filtered blood product from the filter to the collection bag.

44. The system of claim 39 wherein the first and second conduits are dimensioned to preclude air infiltration into the filter once the system is in operation.

45. A method of continuously filtering a blood product through a system, the method comprising steps of:
introducing the blood product to the system, the system providing a connector having a first inlet for receiving the blood product, a second inlet and an outlet, a filter having a filter inlet, the filter coupled to the connector outlet, a collection bag coupled to the filter, and a reservoir bag connected to the second connector inlet for temporarily storing received blood product, and providing the blood product through the connector to the filter to maintain continuity in filtration,
wherein the reservoir bag and the collection bag each include a bottom, the reservoir bag and the collection bag being constructed and dimensioned to enable positioning during filtration such that the connector is below the bottom of the collection bag, and the bottom of the reservoir bag is above the bottom of the collection bag;
filtering the blood product through the system; and
collecting the filtered blood product in the collection bag.

46. The method of claim 45 wherein the connector is a Y connector, the filter is a leukoreduction filter and the blood product comprises blood platelets.

47. The method of claim 45 wherein the system further comprises a first conduit disposed on the first connector inlet for fluidly communicating the received blood product to the connector inlet, and a second conduit disposed between the connector outlet and the filter inlet.

48. The method of claim 47 wherein the system further comprises a third conduit disposed between the reservoir bag and the second connector inlet for fluidly communicating the received blood product from and back into the connector through the second connector inlet.

49. The method of claim 47 wherein the system further comprises a fourth conduit disposed between the filter outlet and the collection bag for fluidly communicating filtered blood product from the filter to the collection bag.

50. The method of claim 47 wherein the first and second conduits are dimensioned to preclude air infiltration into the filter once the system is in operation.

51. The method of claim 45 wherein the collection bag includes a bottom, and the connector is above the bottom of the collection bag when the collection bag is suspended, but below the fluid level in the collection bag after a first cycle.

52. A method of continuously filtering a blood product through a system, the method comprising steps of:
introducing the blood product to the system, the system providing a connector having a first inlet for receiving the blood product, a second inlet and an outlet, a first conduit disposed on the first connector inlet for fluidly communicating the received blood product to the first connector inlet, a filter having a filter inlet, the filter coupled to the connector outlet, a second conduit disposed between the connector outlet and the filter inlet a collection bag coupled to the filter for collecting filtered blood product, and a reservoir bag connected to the second connector inlet for temporarily storing received blood product, and providing blood product through the connector to the filter to maintain continuity in filtration,
wherein the reservoir bag and the collection bag each include a bottom, the reservoir bag and the collection bag being constructed and dimensioned to enable positioning during filtration such that the connector is below the bottom of the collection bag, and the bottom of the reservoir bag is above the bottom of the collection bag;
filtering the blood product through the system; and
collecting the filtered blood product in the collection bag.

53. The method of claim 52 wherein the connector is a Y connector, the filter is a leukoreduction filter and the blood product filtered comprises blood platelets.

54. The method of claim 52 wherein the collection bag includes a bottom, and the connector is above the bottom of the collection bag when the collection bag is suspended, but below the fluid level in the collection bag after a first cycle.

55. The method of claim 52 further comprising a third conduit disposed between the reservoir bag and the second connector inlet for fluidly communicating the received blood product from and back into the connector through the second connector inlet.

56. The method of claim 52 further comprising a fourth conduit disposed between the filter outlet and the collection bag for fluidly communicating filtered blood product from the filter to the collection bag.

57. The method of claim 52 wherein the first and second conduits are dimensioned to preclude air infiltration into the filter once the system is in operation.

58. A system for continuously filtering a blood product comprising:
means for receiving the blood product;
means for filtering the blood product received in the receiving means;
means for collecting filtered blood product from the filtering means; and
variable volume means for temporarily storing received blood product joined by connecting means between the means for receiving blood product and the means for filtering blood product, and providing the received blood product to the filtering means to maintain continuity in filtration
wherein the variable volume means and the means for receiving blood product each include a bottom, the variable volume means and the means for receiving blood product being constructed and dimensioned to enable positioning during filtration such that the connecting means is below the bottom of the means for receiving blood, and the bottom of the variable volume means is above the bottom of the means for receiving blood.

59. The system of claim 58 further comprising a first means disposed on the receiving means for fluidly communicating the blood product to the receiving means, a second means disposed between the receiving means and the filter means for fluidly communicating the received blood product to the filter means, a
third means disposed between the temporary storing means and the receiving means for communicating the received blood product temporarily stored in the temporary storing means to the filter means, and a fourth means disposed between the filter means and the collecting means for fluidly communicating the filtered blood product from the filtering means to the collecting means.

* * * * *